United States Patent [19]

Cordera

[11] Patent Number: 5,005,431
[45] Date of Patent: Apr. 9, 1991

[54] FLOWABLE MATERIAL DISTRIBUTION SAMPLING METHOD AND DEVICE

[75] Inventor: Robert J. Cordera, East Amherst, N.Y.

[73] Assignee: Nabisco Brands, Inc., East Hanover, N.J.

[21] Appl. No.: 356,770

[22] Filed: May 25, 1989

Related U.S. Application Data

[62] Division of Ser. No. 163,539, Mar. 3, 1988, Pat. No. 4,873,103.

[51] Int. Cl.⁵ .............................................. G01N 1/00
[52] U.S. Cl. ................................................. 73/863.53
[58] Field of Search ................... 73/3, 863.31, 863.41, 73/863.51–863.53, 863.91, 863.92, 196, 202; 99/342; 426/233, 289

[56] References Cited

U.S. PATENT DOCUMENTS

| | | | |
|---|---|---|---|
| 3,333,648 | 8/1967 | Dodd | 177/55 |
| 3,487,427 | 12/1969 | Cahill | 73/421 |
| 3,902,370 | 9/1975 | Cahill | 73/421 |
| 3,943,771 | 3/1976 | Handa | 73/424 |
| 4,209,537 | 6/1980 | Wood | 426/233 |
| 4,522,076 | 6/1985 | Shimokawa | 73/863.41 |
| 4,574,645 | 3/1986 | Allen et al. | 73/863.51 |
| 4,808,424 | 2/1989 | Wadell | 426/289 |

FOREIGN PATENT DOCUMENTS

| | | | |
|---|---|---|---|
| 2458783 | 6/1976 | Fed. Rep. of Germany | 73/863.53 |
| 0643770 | 1/1979 | U.S.S.R. | 73/863.53 |
| 1231421 | 5/1986 | U.S.S.R. | 73/863.41 |

*Primary Examiner*—Robert Raevis

[57] ABSTRACT

The distribution of flowable material falling onto a lower surface containing goods which are in the process of being baked can be periodically determined by disposing a multi-sectioned sampling device below the device that is distributing the flowable material to collect a representative sample of the flowable material, and then to analyze the amount of flowable material in each section of the multi-sectioned sampling device. When the flowable material is a solid or a liquid the multi-sectioned device is a multi-chambered device. When the flowable material is a viscous liquid the multi-sectioned device is an array of plates held in a framing.

14 Claims, 2 Drawing Sheets

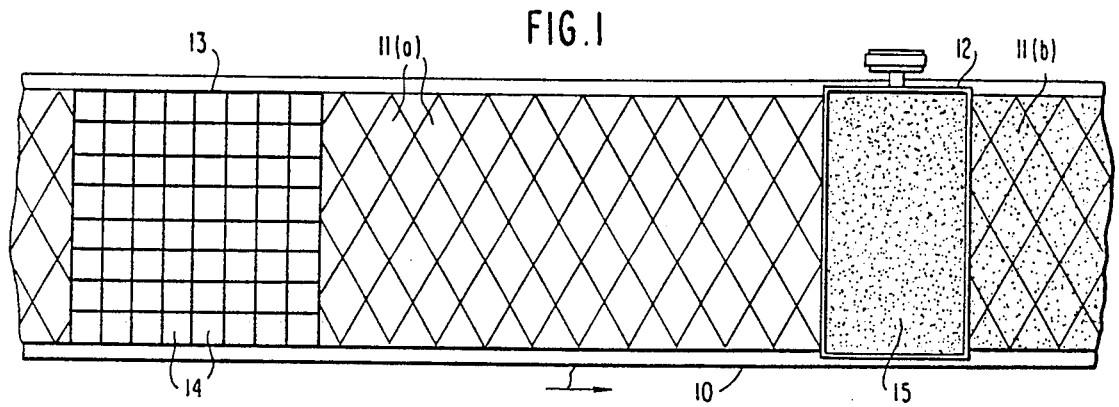
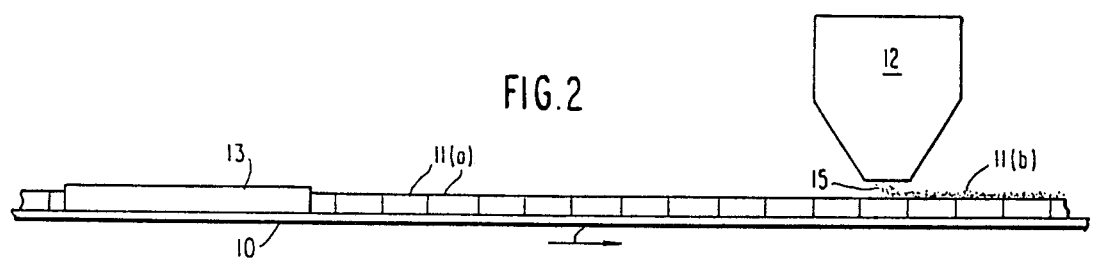
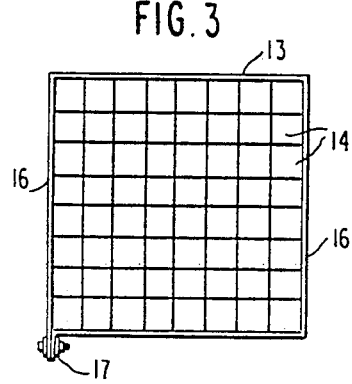
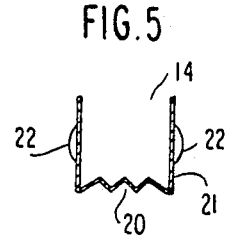
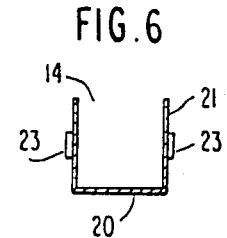
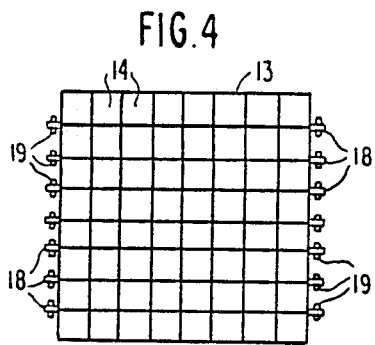
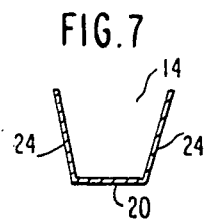
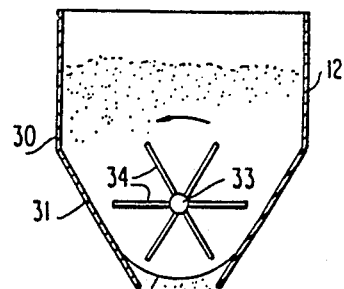

FLOWABLE MATERIAL DISTRIBUTION SAMPLING METHOD AND DEVICE

BACKGROUND OF THE INVENTION

This is a divisional application of application Ser. No. 163,539, filed Mar. 3, 1988, now U.S. Pat. No. 4,873,103.

This invention relates to a baking method and apparatus for determining the distribution of flowable material that is being deposited by gravity onto a surface that is disposed below the apparatus that is distributing the flowable material. More particularly, the present invention relates to a sampling method and device to determine the distribution of salt, spices, flavorants, oils, oil-solid mixtures, water-solid mixtures, icings, enrobing coatings and other related coatings that are deposited onto food articles that have been baked, or that are to be baked, and that are being conveyed below the device distributing the flowable material.

In the production of many baked food items such as cereals, cookies, crackers, biscuits, candies and snack products, various flowable substances are deposited onto the food item during its production. These materials are deposited both before and after baking. Regardless of when applied, it is important that the application be uniform across the entire food product. As the food product passes on a conveyor located below the device that is distributing the flowable material, a preset amount of the solid, liquid or mixed coating is allowed to flow by gravity downward onto the food product. This application of the flowable material must be uniform across the full width of the food product located on the conveyor belt and must be uniform along the length of the food product as it moves along the conveyor belt. Any significant variations will cause the final product to have a varying taste and/or appearance. This creates a problem since the product is a single product that is packaged under a single brand name. Consumers have usually developed a taste for a particular product. Consumers are also usually well aware of the appearance that the product should have when it is to be consumed. Consequently, it is important that all of the product preparation steps be kept as constant as possible. This includes the raw materials that are used, mixing techniques, baking procedures, and as pointed out above, the application of various coatings.

A convenient manner in which to deposit a solid flowable material that is passing below on a conveyor belt is to apply the material by gravity feed That is, the flowable material drops downwardly by gravity after having been metered through a dispenser. For solids such dispensers can be of a type where the material is held in an elongated hopper where the length of the hopper is at least equal to the width of the conveyor belt. The hopper will usually have a truncated V-shape with a series of holes in the lower truncated end whereby flowable material can exit the dispenser. Also located in the dispenser will be a means to agitate the flowable material to assure that it does not pack and agglomerate. In many cases this agitating means will consist of a rotating shaft that carries a series of projections or tines. In the alternative, this rotating shaft can carry a plurality of linear or spiral scraper flanges along the entire length of the shaft.

A method for applying a liquid is to provide a linear nozzle that extends the width of the conveyor belt. This linear nozzle is essentially a tubing with a narrow slit. The tubing will have a length at least equal to the width of the conveyor belt. The liquid will fall through this slit with operation of the nozzle being at atmospheric pressure or at a slightly elevated pressure. The liquid, after leaving the nozzle, will fall downwardly by gravity.

When the substance to be applied is a fairly viscous liquid it can be extruded downwardly from an overhead mounted linear extruder. The extruder will have an extrusion head that is the width of the conveyor belt. The viscous liquid extrudes through an opening of a set dimension and is deposited by gravity onto a surface disposed below the extruder head.

Regardless of the flowable material dispenser that is used, and the technique that is used to keep the flowable material mixed and uniformly flowing from the dispensing region, there is always the need that the flowable material be uniformly distributed from the dispenser onto the product that is passing below the dispenser.

The devices of the present invention are directed to periodically determining whether the flowable material dispenser is functioning properly. This device in the embodiment to sample solid and liquid materials consists of an array of chambers that from time-to-time pass below the dispenser. The array of chambers will collect a representative sample of material from the dispenser. Each chamber will collect a certain amount of material. If the dispenser is dropping flowable material uniformly across the conveyor belt, each chamber will contain essentially the same amount of flowable material. The amount of flowable material in each chamber is determined by weighing each of the chambers to determine the amount of flowable material in each chamber. In the alternative, various wet chemistry techniques can be used. For instance, if the flowable material is salt, a given amount of water can be added to each chamber and the chloride ion or sodium ion concentrations determined Or, if the flowable material has a color, a solvent can be added and the amount of flowable material in each chamber determined photometrically against known standards. Yet other analytical techniques can be used.

When the flowable material is a viscous liquid such as a liquid/solid mixture, the sampler device will be a plurality of flat plates that are held together in a frame. Each flat plate will usually be approximately of the same size as the item onto which the viscous flowable material would be deposited. After the material has been deposited onto the sampler, the sampler is then dismantled and each of the plurality of flat plates is analyzed by weighing to determine the weight of the viscous material deposited onto each part of the sample.

The primary objective is to be able to periodically determine the operation of a flowable material dispenser without having to stop the production of the product. It is important that the dispenser, nozzle or extruder continuously dispense a uniform amount of material. During the operation of the product line there is a constant visual inspection of this part of the process However, visual techniques are not fully effective. The prior art has not extensively addressed this problem.

U.S. Pat. No. 3,487,427 discloses a method and apparatus for sampling ore In the method disclosed in this patent, sample collectors move along a conveyor belt and receive from a loading station the same ore material that is otherwise being deposited onto the conveyor belt. The sample collectors extend across the full width of the conveyor belt. In the method described in this patent the sample collectors would be arranged at various intervals determined by the frequency of sampling that is desired. However, the sample collector of this patent consists of a single chambers that would collect a sample so that the distribution of a material being deposited downwardly can be determined.

U.S. Pat. No. 3,902,370 discloses a sample collector. This is an open-topped, single chamber sample collector which is specially designed to be placed on a conveyor belt and is adapted to receive flowable material which is freely falling downwardly onto the conveyor belt. The sampling container consists of a curved bottom portion but with parallel side walls and end walls. This sample collector also has additional structure at the front and rear ends of the sample collector in order to stabilize the sample collector on the conveyor belt. This sample collector being of a single chamber type would not provide data on the distribution of a material being dispensed via a gravity feed.

U.S. Pat. No. 3,943,771 discloses a sampling device for sampling a powder that is flowing freely down through a conduit This sampling device consists of a rotating disk which extends partially into the conduit and thereby collects some of the material as a sample. As the disk rotates, the material is passed under a viewing window for inspection. After inspection, the sample is returned to the conduit and will become a part of the product stream. This patent does disclose a method for sampling a downwardly flowing flowable material. However, structurally and operationally it will not determine the distribution of a flowable material over a given area.

U.S. Pat. No. 4,574,645 discloses an apparatus and a downwardly. The apparatus consists of a tubular device which extends into a conduit. The tubular device has an opening disposed such that when the tubular device is rotated to a first position it collects downwardly flowing material and deposits this downwardly flowing material into a container which is exterior to the conduit in which the material is being sampled. When this tubular device rotated about 180°, a baffle prevents flowable material from flowing into the tubular device and thus a sample is not taken at that point in time. Using this device, samples can be taken periodically of a material that is flowing downwardly through a conduit. Samples that are being taken are deposited into a single sampling container rather than the use of an array of sampling containers.

U.S. Pat. No. 4,522,076 discloses a method for collecting samples of material from a conveyor belt. The method has the advantage of sampling the full width of the conveyor belt This method consists of the use of a collector conveyor belt for collecting a desired sample. After a sample has been collected, the collector conveyor belt is retracted from the region of the main conveyor belt so that the conveyor belt can continue to deliver the material to a product station. However, this method will collect a single sample rather than a distribution of a downwardly falling material.

Russian Patent 789061 discloses a sampler for taking samples of free-falling materials. In this device, a material such as a flowable material is falling downwardly through a conduit. A sampler is disposed within the conduit, which sample has a slotted end piece. This slotted end piece is moved across the flow of the falling material in order to gather a sample. The sampler is in the shape of a parallelogram. This device is adapted for continuously taking samples of material and for providing these samples for evaluation exterior to the conduit in which the flowable material is flowing. Although this patent discloses the sampling of a downwardly flowing flowable materials, it does not use a plurality of sampling containers and would not provide data on the distribution of a particulate material that is being deposited by gravity onto a lower surface.

BRIEF SUMMARY OF THE INVENTION

This invention comprises a method and apparatus for determining the distribution of a flowable material that is applied from a gravity type of dispenser that is located above a product. In particular, the invention is directed to a method and apparatus that can be used to determine the amount of flowable material such as salt, spices, flavorants, oils, oil-solid mixtures, water-solid mixtures, icings, enrobing coatings and the like that are deposited onto a food product either before or after the food product is baked. The method consists of periodically passing below the dispenser a sampling device that consists in one embodiment of an array of chambers and in another embodiment of a plurality of essentially flat plates. The array of chambers or flat plates would be of a size of a representative sample of the articles that are to receive a coating of flowable material. That is, the sampling device would cover the full width of the conveyor belt on which the food product is moving and a designated length of the conveyor belt to get a statistically representative sample.

When the sampling device is an array of chambers, the chambers are held together by mechanical or magnetic means. The individual chambers are usually of the same size, but this is not a requirement. The chambers can be cubical or rectangular and can have straight or angled sizes. Also, the bottom of each chamber can be flat or shaped. By shaping the bottom of the chambers and/or angling the sides of the chambers, the tendency of solid flowable material to land in one chamber and bounce to another chamber can be minimized.

Each chamber can be weighed to determine the amount of flowable material in each chamber and thus the distribution of flowable material. In addition, the individual chambers can contain a liquid in which the flowable material is soluble. This can be water, an organic solvent or a mixture of liquids. The liquid can be in the individual chambers while the array of individual chambers is passing below the dispenser, or may be added later to analyze for the amount of flowable material in each chamber. Essentially, any analytical technique can be used. When salt is being dispensed, the chloride ion or sodium ion concentration can undergo analysis. When the flowable material has a particular color, the concentration of the flowable material can be determined photometrically from a known standard. The net result is a method to accurately determine the distribution of a flowable material that is being deposited by gravity onto a product on a lower surface.

When the sampling device is a plurality of essentially flat plates that are to receive a viscous material, the essentially flat plates will be held in an array in a frame. The flat plates, like the array of chambers, will receive the downwardly falling flowable material. In many instances this will be a fairly viscous extruded material. The essentially flat plates become coated with the material. The holding frame is then dismantled and each of the plurality of essentially flat plates is weighed or otherwise analyzed in order to determine the amount of viscous material on each plate.

From the data derived from the sampling it can quickly be determined whether the product being manufactured is within specification. If not, the reason for the deviation from the specification can be determined. These samplers and these sampling techniques also provide valuable information with regard to the operational state of various units of equipment. Equipment that is illustrating wear can be replaced or repaired before out-of-specification products are produced.

DESCRIPTION OF THE DRAWINGS

FIG. 1 is a top plan view of a baking line with a solid particulate distribution device and with the multi-chambered sampler means.

FIG. 2 is a side elevational view of a baking line with a solid particulate distribution device with multi-chambered sampler means of FIG. 1.

FIG. 3 is a top plan view of the multi-chambered sampler device showing the chambers maintained in an array using an encircling strap.

FIG. 4 is a top plan view of the multi-chambered sampler device showing the chambers maintained in an array using fastening rods.

FIG. 5 is an elevational view of a single chamber used with the rod joining means of FIG. 4 and which further has an uneven bottom surface.

FIG. 6 is an elevational view of a single chamber showing a chamber having sides that are perpendicular to the bottom surface and wherein the chambers are maintained in an array by magnetism.

FIG. 7 is an elevational view of a single chamber showing a chamber having sides that are at an angle of greater than 90° to the bottom surface.

FIG. 8 is an elevational view of a single chamber showing a chamber that has side walls in two different orientations.

FIG. 9 is a side elevational view in a section of the solid particulate distribution device of FIG. 1.

DETAILED DESCRIPTION OF THE INVENTION

Figure 10:
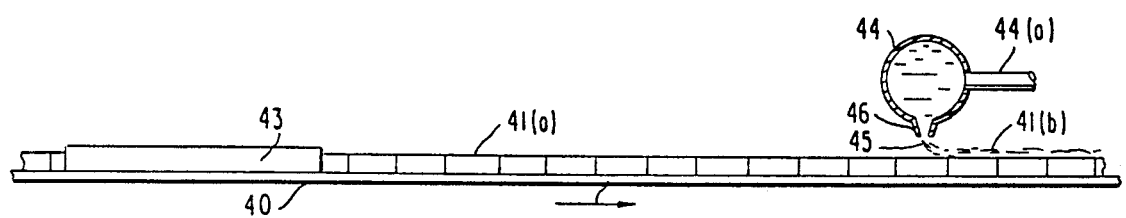
FIG. 10 is a side elevational view of a baking line with a viscous liquid distribution device and a plate array sampling device.

As has been noted, in the production of many food products there is a step of applying a flowable material to the food product. This is applied to the food product before or after it has been baked. In general, the food product passes along on a continuous conveyor with a dispenser mounted above the conveyer. The dispenser meters a certain amount of flowable material downwardly onto the food product as it passes beneath the dispenser. By adjusting the dispensing rate of the dispenser and the speed of the conveyor belt, a certain known amount of the flowable material can be deposited onto the food product. The various flowable materials that are usually deposited onto food products consist of salt, spices, flavorants, oils, oil-solid mixtures, water-solid mixtures, icings, enrobing materials and the like. The food products onto which these flowable materials can be deposited include cereals, cookies, crackers, biscuits, candies, cakes and various snack items. In the present process and apparatus, there is provided a technique for rapidly and accurately determining the distribution of the flowable material that is being dispensed. It is important that the flowable material be dispensed uniformly across the product on the conveyor belt and that it be dispensed uniformly onto the product linearly along the conveyor belt.

In the drawings, FIGS. 1 through 9 are directed to the embodiment where a plurality of individual sampling chambers are used. Such individual sampling chambers would be used where the dispensed material is either a solid or a liquid. In either case the individual chambers would each receive a representative sample of the material that is falling downwardly by gravity. The dispenser in FIGS. 1, 2 and 9 is a dispenser for a solid particulate material. The dispenser of FIGS. 10 and 11 can be used for viscous liquids which are extruded from the nozzle head under pressure.

In FIG. 1, there is shown a conveyor belt 10 which carries a product 11(a) that is to be coated. The product is assumed to be crackers. The crackers can be in a baked form at this time or at a point in the process where they are to enter the baking ovens. Mounted above the conveyor belt 10 is particulate material dispenser 12. This particulate material dispenser 12 will dispense a solid material 15 such as salt, spices, or flavorants across the full width of the conveyor belt. In this way, the cracker product that is passing beneath the dispenser receives a uniform amount of salt, spice, or flavorants. The coated baked product is designated as 11(b). The uncoated product is designated as 11(a). Located upstream from the dispenser is sampler 13. Sampler 13 consists of an array of separate chambers 14. This sampler 13 moves along the conveyor belt and will pass beneath the particulate material dispenser 12. As it passes beneath particulate material dispenser 12, it will receive particulate material into each of the individual chambers 14. Each of the chambers 14 will receive particulate material that would have fallen onto a specific area beneath the dispenser. In the present instance, this would have been one or more individual crackers. After the sample 13 has passed beneath the dispenser 12 it is removed from the conveyor belt line and forwarded for analysis. Analysis will consist of determining the amount of particulate material that has fallen into each of the individual chambers.

FIG. 2 is a side elevational view of the conveyor belt assembly of FIG. 1. As in FIG. 1, the conveyor belt assembly is operated at the same speed when the sample is being collected as when the baked or to be baked product is being coated with the particulate material. After the sampler device 13 has passed beneath the dispenser and has collected particulate material 15 into each of the individual chambers, it is then removed from the conveyor belt line and, as described, forwarded for analysis.

The sampler 13 must extend laterally across the full conveyor belt. This is necessary in order for the sampler to receive a representative sample when it passes beneath the dispenser 12. The sampler 13 can be of essentially any desired length. However, in order to generate statistically accurate data the sampler device will extend from about 6 inches to about 48 inches in length, and preferably about 12 to 36 inches in length. In this way, a statistically accurate sample can be gathered. Each of the individual chambers 14 will be of the same size, although this is not absolutely necessary. However, it is desirable that the chambers be of a size that is the same as the individual cracker, biscuit or the like that is being coated. These individual chambers can be cubical in shape or have a rectangular opening. In FIG. 3, the individual chambers are shown to be cubical in shape. Also in FIG. 3, the array of sample chambers 14 are shown to be held together into an array by means of strap 16. Strap 16 surrounds the array of sample chambers 14 and maintains them in a defined position. At one corner, the straps are fastened together by means of a fastener 17. Fastener 17 can be of any conventional type, such as a conventional screw and nut arrangement. After the sampler 13 has been removed from the conveyor line, the holder strap 16 is released and each of the individual chambers is weighed or otherwise analyzed for its contents.

FIG. 4 shows a similar sampler device as is shown in FIG. 3 except that the individual chambers 14 are maintained in the array-type of arrangement by means of a plurality of rods 18 that pass from one end of the array to the other end of the array. Each end of the rod is threaded and contains a nut locking means 19 which maintains the individual chambers 14 in position. The rod 18, as shown in FIG. 5, will extend through side tabs 22 of each of the individual chambers. The side tabs 22 are offset so that they can be aligned and a rod passed through a series of these side tabs. Also shown in FIG. 5 is the embodiment of an individual chamber having an essentially cubical shape. This view also shows the embodiment of an irregular bottom surface 20 and perpendicular side walls 21.

FIG. 6 shows an embodiment of the chamber 14 wherein the side walls 21 carry a magnetic material 23 for attaching the individual chambers one to the other.

FIG. 7 shows an embodiment of the individual chambers 14 wherein the side walls 24 form an angle with the bottom of the chamber 20 that is greater than 90°. In this embodiment, flowable material that falls downwardly will be deflected off the walls 24 and down into chamber 14.

FIG. 8 shows an embodiment of the individual chamber 14 wherein the lower part 26 of the side wall forms an angle of less than 90° with the bottom 20, while the upper portion of the side wall 25 extends outwardly. That is, if wall portion 25 were to be extended downwardly to the bottom 20 it would form an angle of greater than 90° with the bottom of the individual chamber. In this embodiment, flowable material, as it falls downwardly, will generally tend to remain in the individual chamber rather than to potentially bounce out and enter into another individual chamber.

FIG. 9 is a cross-sectional view of the particulate material dispenser of FIG. 1. The dispenser consists of a V-shaped trough 12 having side walls 30 and 31. At the bottom of the V-shaped trough there is an opening 32 to permit the particulate material to flow downwardly. Within the trough there is a rotating shaft 33 which contains a plurality of scraper bars 34 which are used to agitate the particulate material and to move the particulate material by baffle 35 which contains openings of a size to permit particulate material to flow downwardly. This FIG. 9 sets forth one type of a device that can be used for depositing a particulate material by gravity downwardly onto a surface. However, there are many other commercial devices that have been designed for this purpose and that are in general commercial usage. This present invention is not restricted to the use of any one particular dispenser device. Any dispenser device can be used, as can any conveying means.

Figure 11:
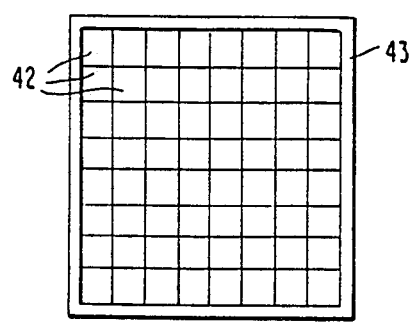
FIG. 11 is a top plan view of a plate array sampling device.

FIG. 10 shows a side elevational view of the sample device being used to sample a liquid material. In this view, 41(a) designates the uncoated product, while 41(b) designates the coated product. The conveyor belt 40 moves the plate of FIG. 11 toward the dispenser 44. The dispenser flows liquid 45 downwardly onto the product. The coated product would then move on to packaging. FIG. 11 is a top plan view of the plurality of plates 42 which are held in an array by means of frame 43. In the operation of the sampler device, liquid is supplied to linear nozzle 46 of dispenser 44. The nozzle 46 consists of a slit which extends the width of the conveyor belt. This slit has an opening from about 0.0156 inch to about 0.5 inch. Depending on the viscosity of the liquid, a positive pressure may be needed in order to have the liquid 45 flow continuously from the nozzle. This can be accomplished by pumping the liquid into dispenser 44 and maintaining a positive pressure in dispenser 44. The amount of pressure that would be used would depend on many factors. These include the viscosity of the liquid and the thickness of the desired coating.

After the plurality of plates pass under dispenser 44 and get coated, they are removed for analysis. Analysis will consist of removing the individual plates 42 from the frame 43 and weighing each of the plates. The weight of each plate will then provide a good statistical overview of the operation of the liquid dispenser.

As has been set out above, the sampling device consists of an array of individual sampling chambers or sampling plates. These sampling chambers and plates can be of essentially any size. However, it is preferred that the sampling chambers have an opening, and the sampling plates have a size, of at least about one square inch to about 36 square inches, and preferably about 4 to 16 square inches. Generally, the upper opening will be square in shape although this is not a requirement. Rectangular or other shape openings of the chambers and shape of the plates could also be used. As noted above, it is preferred that the openings and that the shape of the plates be of a size and shape as the item that is to be regularly coated.

The individual chambers can contain a liquid in which the flowable material is soluble at the point in time when the sampling device is passed under the flowable material dispenser. In such a case, the material will fall downwardly into the liquid. Besides permitting for a subsequent chemical or photochemical analysis of the flowable material, the liquid will have a tendency to keep the particulate material within the chamber into which it falls. That is, when an individual chamber contains a liquid there is a significantly decreased tendency for the flowable material that falls into that chamber to bounce out of that chamber. In the chemical analysis for the flowable material, various properties of the flowable material can be used in the analytic procedure. For instance, when the flowable material is salt, an analysis can be conducted for the chloride ion or sodium ion concentration of the solution in each of the individual chambers. This will then yield the amount of salt that dropped into that individual chamber. For spices and flavorants, it may be more useful to use photochemical techniques. For instance, when a strawberry, grape, lemon, or orange flavorant is being used, these can be allowed to drop into an aqueous or an acidic aqueous solution in which the flavorant is soluble and the degree of color of the solution compared against a standard in order to yield the concentration of the flavorant in that particular individual chamber. Yet other known wet chemical techniques can be used in the place of those herein discussed. Such techniques are known and are within the skill of those in the art.

An advantage to the present sampling device is that it can be used repeatedly after cleaning. This provides a savings. And, of course, the prime advantage will be able to closely monitor the product quality and the functioning of the dispensers and other machinery.

These present processes for determining the distribution of flowable material as applied to various foodstuffs will now be set forth in more detail with specific reference to the following examples.

EXAMPLE 1

This example illustrates the sampling of salt that is being dropped by gravity from an overhead mounted salter. The salt during a production run is deposited onto crackers that are passing below on a conveyor belt.

A sampler is chosen that has openings about the size of the individual crackers. The sampler has 5 rows placed side by side. There are 38 chambers in each row. The overall dimensions of the sampler are 12.5 inches in width and 47.5 inches in length. Each chamber of the sampler measures 2.5 inches in length and 1.25 inches in width and covers the full width of the conveyor belt.

The conveyor belt is started and run at 1 foot per second and the overhead salter is started. After 5 minutes of operation for the salter to reach steady state operation, the sampler is placed before the salter onto the conveyor belt. The sampler moves under the salter and the falling salt enters into the individual chamber that is passing below. After the sampler has passed the salter it is removed from the conveyor belt and sent for analysis. The sampler is dismantled and each of the individual chambers is weighed to determine the amount of salt that has fallen into that individual chamber. It is found that the individual chambers contain from 0.04 gms of salt to 0.077 gms of salt. This provides an average chamber content of 0.059 gms. The standard deviation is 0.0086 gms.

This is determined to be acceptable for the production of the present cracker product.

What is claimed is:

1. An apparatus for coating food articles and determining the distribution of a flowable coating material being dispensed onto a moving lower surface containing edible food articles which are to be baked comprising means to uniformly distribute a flowable coating material downwardly onto a continuously moving lower surface, and a multi-sectioned collection means received on said continuously moving surface disposed below said means to distribute said flowable coating material to collect a representative sample of said flowable coating material in each section of said multi-sectioned collection means to determine distribution, wherein said multi-sectioned collection means comprises a plurality of substantially uniform collections chambers and wherein said collection chambers are of a size corresponding substantially to the food articles whereby each sample collected in each section corresponds to an amount of said coating material dispensed onto said food articles.

2. An apparatus for coating and determining distribution of a flowable coating material onto a lower surface as in claim 1 wherein said lower surface is a conveyor with said edible food articles disposed thereon.

3. An apparatus for coating and determining the distribution of a flowable coating material onto a lower surface as in claim 1 wherein the means to determine said flowable material evenly distributes said flowable material onto the edible food articles on said lower surface.

4. An apparatus for coating and determining the distribution of a flowable coating material onto a lower surface as in claim 1 wherein said multi-sectioned collection means consists of an array of plates.

5. An apparatus for coating and determining the distribution of a flowable coating material onto a lower surface as in claim 4 wherein said array of plates is maintained in said array by means of a frame.

6. An apparatus for coating and determining the distribution of a flowable coating material onto a lower surface as in claim 1 wherein said multi-sectioned collection means is comprised of an array of equivalent sized chambers sufficient to collect a representative sample of said flowable material.

7. An apparatus for coating and determining the distribution of flowable coating material onto a lower surface as in claim 6 wherein side walls of each chamber of said multi-chambered collection means are perpendicular to a bottom surface of each chamber.

8. An apparatus for coating and determining the distribution of a flowable coating material onto a lower surface as in claim 6 wherein at least a portion of a side wall of each chamber of said multi-chambered means is at an angle of greater than about 90° to a bottom surface of said chamber.

9. An apparatus for coating and determining the distribution of a flowable coating material onto a lower surface as in claim 6 wherein at least a portion of a side wall of each chamber of said multi-chambered means is at an angle of less than about 90° to a bottom surface of said chamber.

10. An apparatus for coating and determining the distribution of a flowable coating material onto a lower surface as in claim 6 wherein each chamber of said multi-sectioned collection means contain a liquid in which a solid flowable coating material is soluble.

11. The apparatus according to claim 1 wherein said multi-sectioned collection means is substantially the width of the moving lower surface.

12. The apparatus according to claim 1 wherein said multi-sectioned collection means is removably received on said continuously moving lower surface.

13. An apparatus for determining the distribution of a flowable coating material being dispensed from a dispensing means onto a plurality of edible food articles on a continuously moving conveyor surface, said apparatus comprising a multi-sectioned collection means having a plurality of substantially uniform collection chambers, said chambers having a size substantially equal to edible food articles on a continuously moving conveyor, said multi-sectioned collection means having a width substantially equal to the width of said conveyor, wherein said collection means is removably received on said conveyor to collect a representative sample of a coating material continuously dispensed onto said edible food articles whereby a sample collected in each of said chambers correspond substantially to the amount of coating material dispensed onto each edible article.

14. An apparatus for determining the distribution of a flowable edible coating material comprising in combination a continuously moving conveyor to receive a plurality of substantially uniform edible food articles; a dispensing means disposed above said conveyor to uniformly dispense a coating of flowable edible coating material onto said food articles, and; a multi-sectioned collection means removably received on said conveyor to be conveyed simultaneously with said food articles below said dispensing means to collect a sample of said coating material to determine distribution of said coating material, wherein said collection means comprises a plurality of substantially uniform collection chambers, each chamber having a dimension substantially equal to the edible food articles whereby each chamber collects an amount of coating material substantially equal to an amount dispensed onto said edible food article, and wherein said collection means is substantially the full width of said conveyor.

* * * * *